US00PP35482P2

(12) United States Plant Patent
Bailey

(10) Patent No.: US PP35,482 P2
(45) Date of Patent: Nov. 14, 2023

(54) ***HEUCHERA* PLANT NAMED 'PP2020'**

(50) Latin Name: ***Heuchera* hybrid**
Varietal Denomination: PP2020

(71) Applicant: Matthew Bailey, Ankeny, IA (US)

(72) Inventor: Matthew Bailey, Ankeny, IA (US)

(73) Assignee: RIJNBEEK AND SON PERENNIALS EXPORT B.V., Boskoop (NL)

( * ) Notice: Subject to any disclaimer, the term of this patent is extended or adjusted under 35 U.S.C. 154(b) by 0 days.

(21) Appl. No.: 18/115,863

(22) Filed: Mar. 1, 2023

(30) Foreign Application Priority Data

May 18, 2022 (QZ) ..... PBR 2022/1258

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Heuchera* plant named 'PP2020' that is characterized by its foliage that is gray-green to grey in color with dark green veins on the upper surface and purple in color on the lower surface that become more purple in late summer and fall, its cold winter hardiness at least to U.S.D.A. Zone 4, and its strong garden performance.

3 Drawing Sheets

Botanical classification: *Heuchera* hybrid.
Cultivar designation: 'PP2020'.

CROSS REFERENCE TO A RELATED APPLICATION

This application claims priority to European Community Plant Variety Office (CPVO) Plant Breeder's Rights Application No. No. 2022/1258, filed May, 18, 2022. The Applicant received the information for the Plant breeders' rights application directly from the Inventor.

BACKGROUND OF THE INVENTION

The present invention relates to a new and distinct cultivar of *Heuchera* of hybrid origin, botanically known as *Heuchera* 'PP2020', and is hereinafter referred to by its cultivar name 'PP2020'.

The new cultivar arose from an ongoing breeding program conducted by the Inventor in Ankeny, Iowa. The goal of the breeding program is to develop new cultivars of *Heuchera* with improved winter hardiness and garden performance. The new cultivar resulted from a cross made between unnamed and unpatented proprietary plants from the Inventor's breeding program in 2011. The female parent was an open pollinated seedling of 'Ruby Bells' (not patented) and the male parent was an open pollinated seedling of an unnamed plant of *Heuchera richardsonii*. 'PP2020' was selected as a single unique plant in summer of 2012 from the resulting seedlings.

Asexual propagation of the new cultivar was first accomplished under the direction of the Inventor by division in 2013 in Ankeny, Iowa. Asexual propagation of the new cultivar by division and tissue culture using meristematic tissue has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'PP2020' as a new and unique cultivar of *Heuchera*.

1. 'PP2020' exhibits foliage that is gray-green to grey in color with dark green veins on the upper surface and purple in color on the lower surface that become more purple in late summer and fall.
2. 'PP2020' cold winter hardiness at least to U.S.D.A. Zone 4.
3. 'PP2020' exhibits strong garden performance.

Both parents of 'PP2020' differ from 'PP2020' in having leaves that are dark green in color with silver veins. 'PP2020' can be most closely compared to the *Heuchera* cultivars 'Purple Palace' (not patented) and 'TNHEUFP' (U.S. Plant Pat. No. 26,358). Both 'Purple Palace' and 'TNHEUFP' are similar to 'PP2020' in foliage color. 'Purple Palace' differs from 'PP2020' in having leaves with leaf lobes that are more pointed, surfaces that are more glossy and coloration that are purple-gray throughout the season, and in being less winter hardy. 'TNHEUFP' differs from 'PP2020' in having foliage with leaf lobes that are more pointed, surfaces that are more glossy, and more purple in color on the upper surface and in being less winter hardy with not as strong performance in the garden.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Disclosure of first sale date on the CPVO plant breeder's application refers to distribution of trial plants only. Disclosures include website listing by isu-perennials and Groen Direkt.

BRIEF DESCRIPTION OF THE DRAWINGS

The accompanying color photographs illustrate the overall appearance and distinct characteristics of the new *Heuchera*. The photographs were taken of a plant 8 months in age of the new cultivar as grown outdoors in a 17-cm containers in Boskoop, The Netherlands.

The photograph in FIG. 1 provides a side view of the plant of 'PP2020' in bloom.

Figure 1:
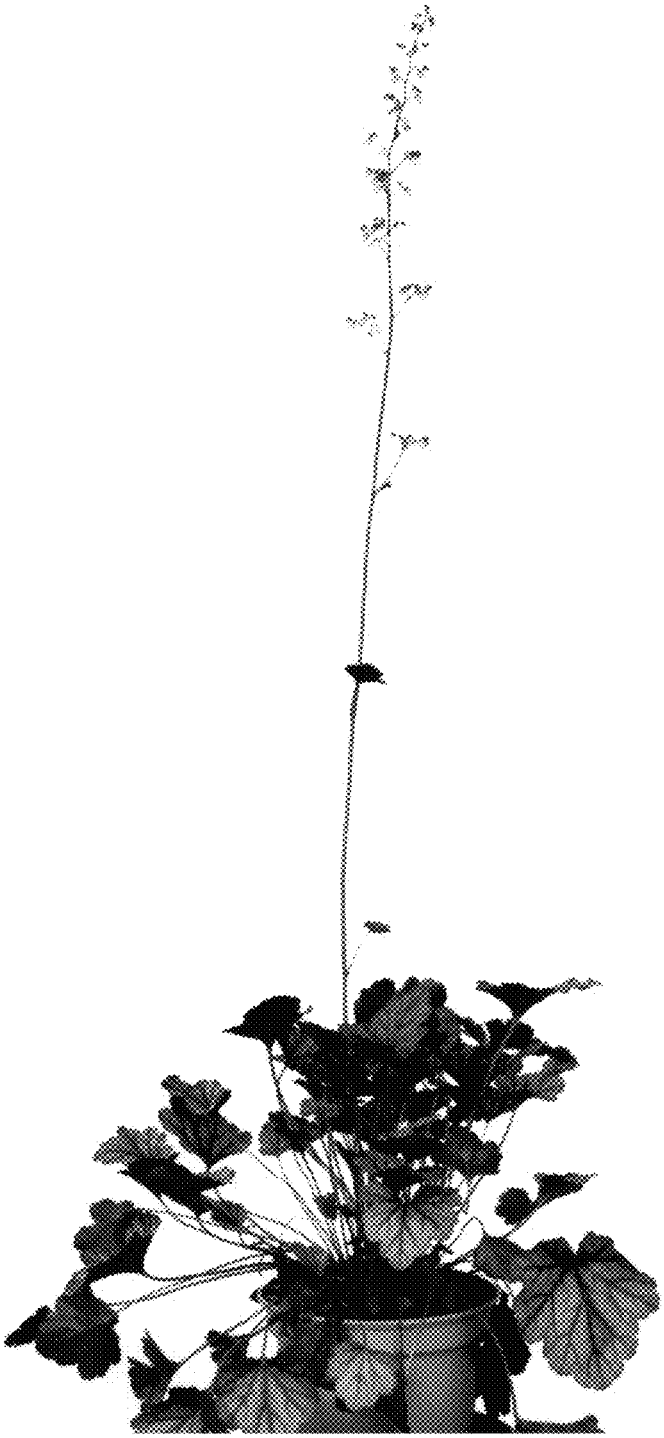
Figure 2:
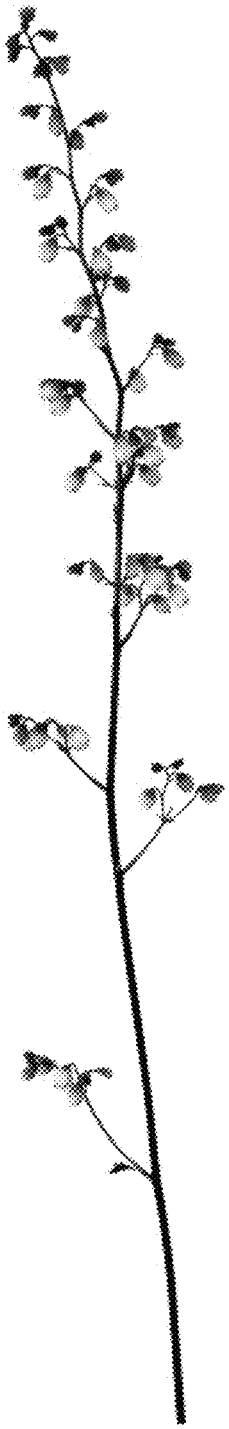

The photograph in FIG. 2 provides a close up of an inflorescence of 'PP2020'.

Figure 3:
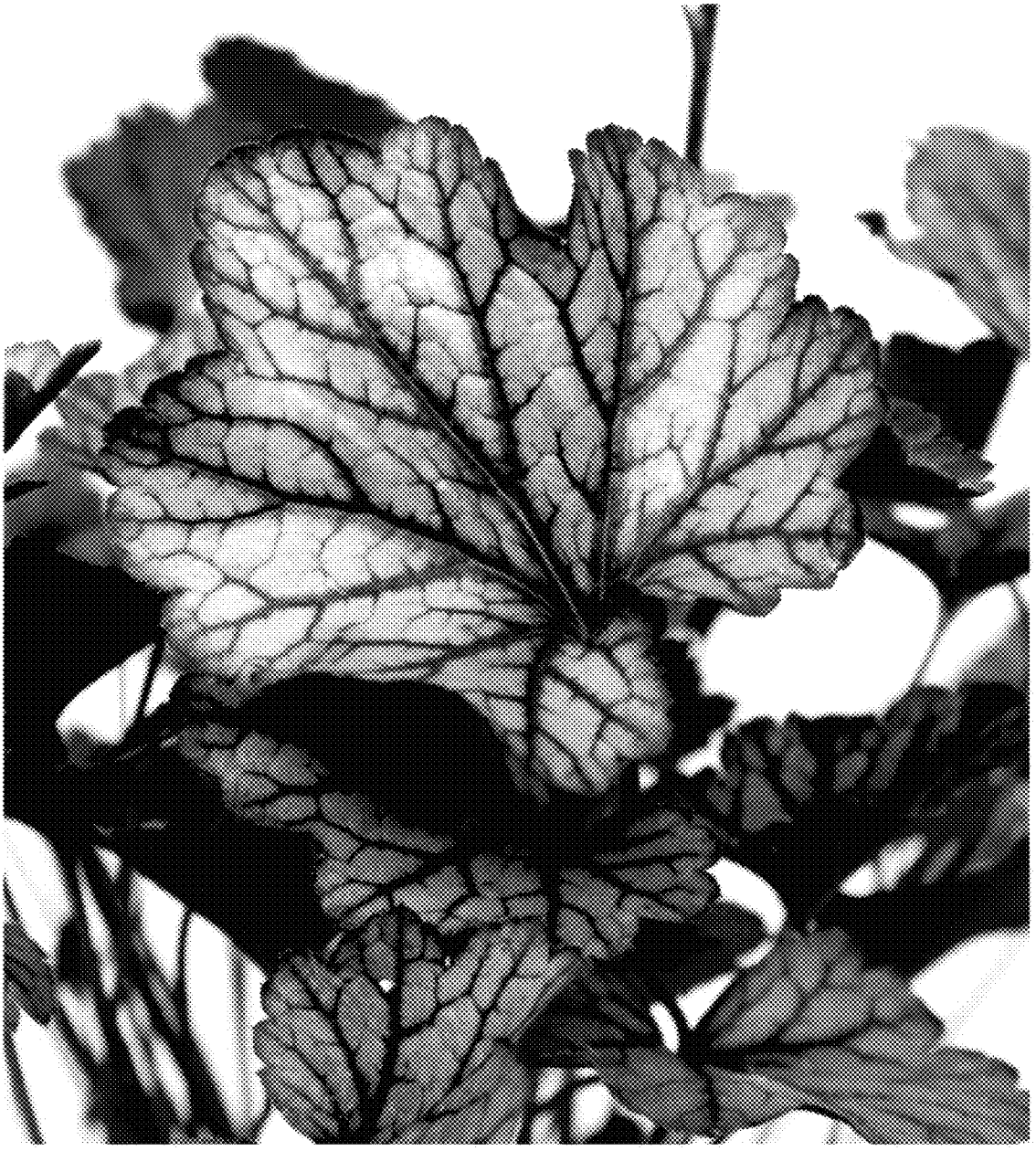

The photograph in FIG. 3 provides a close-up view of the foliage colors of 'PP2020'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 8 month-old plants of the new cultivar as grown outdoors in 17-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—10 to 12 weeks, starting in mid-June in The Netherlands.

*Plant type*.—Herbaceous perennial.

*Plant habit*.—Broadly upright with inflorescences held above the foliage.

*Height and spread*.—An average of 23 cm in height (soil level to top of foliar plane), average of 89.8 cm in height (soil level to top of floral plane) and 48.8 cm in spread.

*Hardiness*.—At least in U.S.D.A. Zones 4 to 9, has performed well in Zone 4 for 9 years of trials.

*Diseases and pests*.—No susceptibility or resistance to diseases or pests has been observed.

*Root description*.—Fibrous roots on woody rootstalks, 158D in color.

*Propagation*.—Division and tissue culture.

*Root development*.—An average of 3 weeks for root initiation and 6 weeks to produce a rooted cutting.

*Growth rate*.—Vigorous.

*Branching habit*.—Flowering stems emerge from basal rosette, an average of 6 rosettes per plant, no lateral branches.

Foliage description:

*Leaf shape*.—Broadly ovate to nearly orbicular in outline, slightly concave.

*Leaf division*.—Simple.

*Leaf base*.—Hastate, lobes free to slightly overlapping.

*Leaf apex*.—Minutely abruptly acute.

*Leaf venation*.—Laciniate, upper surface N189A, tinged 203D, lower surface N79B.

*Leaf margins*.—Crenate with minute, acute tips on each tooth, slightly to moderately undulate.

*Leaf attachment*.—Petiolate.

*Leaf arrangement*.—Alternate in basal rosettes.

*Leaf lobes*.—Lobed, an average of 7 lobes, occasionally 9, shallow in depth, divergent, lobe margins free to touching.

*Leaf surface*.—Upper surface; moderately velvety, smooth, slightly glossy, lower surface; moderately glossy, moderately covered with very short strigose hairs; 0.5 mm and too small to measure color.

*Leaf color*.—Young upper surface; 201A, young lower surface; N79A and 187B, mature upper surface; a blend of N79A and 187B, changing late summer into fall 186A, mature lower surface; N79B.

*Leaf size*.—An average of 10.1 cm in length and 9.9 cm in width.

*Leaf quantity*.—An average of 8 per basal rosette.

*Petioles*.—An average of 19.2 cm in length and 2.25 mm in diameter, medium strength, both surfaces moderately glossy, color; upper surface a blend of N79D and 187D, lower surface 186A, tinged at distal end 182B, sparsely to moderately covered 20 with short soft hairs; an average of 1.5 mm in length, transparent to matching surface color.

*Stipules*.—Leafy stipule at the base of each leaf, average 1.4 cm in length, average 7 mm in width, acute tip, margins ciliate, 186A, margins 156D in color, surfaces glossy.

Flower description:

*Inflorescence type*.—Campanulate, numerous small bell-shaped flowers arranged on panicles on peduncles emerging from a basal rosette.

*Inflorescence size*.—An average of 34.7 cm in height and 6.6 cm in diameter.

*Inflorescence number*.—An average of 1.

*Flower fragrance*.—None.

*Flower quantity*.—Average of 140 flowers per flowering stem.

*Flower lastingness*.—Average of one week.

*Flower buds*.—Obovate in shape, an average of 4.5 mm in length and 2.75 mm in diameter, color; 187B, top 183C, surface is matte and densely covered with very short glandular hairs; an average of 0.3 mm in length and too small to measure color.

*Flower aspect*.—Nodding to slightly outward.

*Flower type*.—Single, campanulate.

*Flower size*.—Average of 8 mm in height, 6 mm in diameter.

*Petals*.—Average of 5, rotate arrangement and implanted in the hypanthium at base, oblanceolate in shape, margin is entire, apex is acute, base is long acuminate, upper and lower surface is glabrous, smooth and matte, an average of 3.5 mm in length and 1.5 mm in width, color when opening and fully open upper and lower surface; 75D.

*Calyx*.—Campanulate, sepals fused to hypanthium, 8 mm in length, 6 mm in diameter.

*Sepals*.—An average of 5, lower 37.5% fused into campanulate hypanthium, short oblong in shape, an average of 7 mm in length and 3 mm in width, margin is entire and fused into hypanthium, apex is obtuse, color; when opening and fully open upper surface 75D, tip 153B to 153C, when opening and fully open lower surface 75D, lower half 63C, tip 177B, main vein 187C, both surfaces are matte and densely covered with very short glandular hairs; an average of 0.2 mm in length and too small to measure color.

*Peduncle*.—An average of 91.5 cm in length and 2.5 mm in diameter, color; 200A, tinged N186C, primary flower aspect 70° to horizontal, secondary peduncle aspect to main peduncle 60°, moderate in strength, surface moderately glossy and densely covered with very short soft glandular hairs; average of 1 mm in length, 155A in color.

*Pedicels*.—An average of 5 mm in length and 0.6 mm in diameter, 200A, tinged N186C in color, pedicels of primary flower aspect straight on top of secondary peduncle, pedicels of secondary and tertiary flowers aspect 60° (0°=straight on top of primary peduncle), moderate in strength, surface is matte and moderately covered with very short soft glandular hairs an average of 0.2 mm in length and too small to measure color.

Reproductive organs:

*Gynoecium*.—Pistils; 2, 4 mm in length, stigma; club-shaped, 0.2 mm in diameter, style; an average of 3.75 mm in length and 75D in color, ovary; 147D in color.

*Androecium*.—Stamens; 5, anthers; ovate in shape, average of 1.5 mm in length, 1 mm in width, 28B in color, filament; 2 mm in length and 155C in color, pollen; low in quantity, 22A in color.

*Seed/fruit*.—No fruit or seeds have been observed to date.

It is claimed:

1. A new and distinct cultivar of *Heuchera* plant named 'PP2020' as herein illustrated and described.

* * * * *